United States Patent
Börmann et al.

(10) Patent No.: US 8,163,216 B2
(45) Date of Patent: Apr. 24, 2012

(54) METHOD FOR PRODUCING A FILM WEB

(75) Inventors: Ludwig Börmann, Babensham (DE);
Günter Schreiner, Schnaitsee (DE)

(73) Assignee: RKW SE, Frankenthal (DE)

( * ) Notice: Subject to any disclaimer, the term of this patent is extended or adjusted under 35 U.S.C. 154(b) by 410 days.

(21) Appl. No.: 11/792,735

(22) PCT Filed: Apr. 26, 2006

(86) PCT No.: PCT/EP2006/003891
§ 371 (c)(1),
(2), (4) Date: Jul. 30, 2007

(87) PCT Pub. No.: WO2006/136226
PCT Pub. Date: Dec. 28, 2006

(65) Prior Publication Data
US 2008/0131681 A1  Jun. 5, 2008

(30) Foreign Application Priority Data
Apr. 26, 2005  (EP) .................................. 05009126

(51) Int. Cl.
*B29C 71/00* (2006.01)
(52) U.S. Cl. ............... 264/234; 264/210.2; 264/211.12; 264/237; 264/288.4; 264/345
(58) Field of Classification Search .............. 428/220; 525/86–87, 240; 264/177.17, 177.19, 211.12
See application file for complete search history.

(56) References Cited

U.S. PATENT DOCUMENTS

| | | |
|---|---|---|
| 3,548,048 A | 12/1970 | Hughes et al. |
| 5,707,478 A | 1/1998 | Fujii et al. |
| 2003/0216518 A1* | 11/2003 | Tau et al. ............... 525/191 |

FOREIGN PATENT DOCUMENTS

| | | |
|---|---|---|
| DE | 3326056 A1 | 1/1984 |
| DE | 3326056 C2 | 1/1993 |
| EP | 0452813 A2 | 10/1991 |
| EP | 0452813 A3 | 10/1991 |
| EP | 0256885 B1 | 4/1993 |
| EP | 0256885 B2 | 10/1997 |
| EP | 0616880 B1 | 5/2000 |
| EP | 0768168 B1 | 4/2002 |
| GB | 2152515 A | 8/1985 |
| GB | 2152516 A | 8/1985 |
| WO | WO 95/32089 | 11/1995 |

OTHER PUBLICATIONS

Yamada, Toshiro (edited by Kanai et al.). "Film Processing". Hanser/Gardner Publications, 1999. pp. 181-209.*

English translation of EP Application No. 96116322.7 filed Oct. 11, 1996; published as EP 0 768 168 A2 on Apr. 16, 1997; Applicant: BP Chemicals PlasTec GmbH.

* cited by examiner

*Primary Examiner* — David Sample
*Assistant Examiner* — Prashant J Khatri
(74) *Attorney, Agent, or Firm* — McCarter & English, LLP; Steven Davis

(57) ABSTRACT

The invention relates to a method for producing a film web during which an initial film web made of thermoplastic polymer material with a polyethylene matrix, in which 1 to 70 parts by weight of polypropylene, with regard to 100 parts by weight of polyethylene matrix, are contained, is, after being heated, guided through a cooled roll gap (7, 8), whereby the initial film web is heated only until the polymer matrix material melts but not to a temperature at which the polypropylene melts.

15 Claims, 1 Drawing Sheet

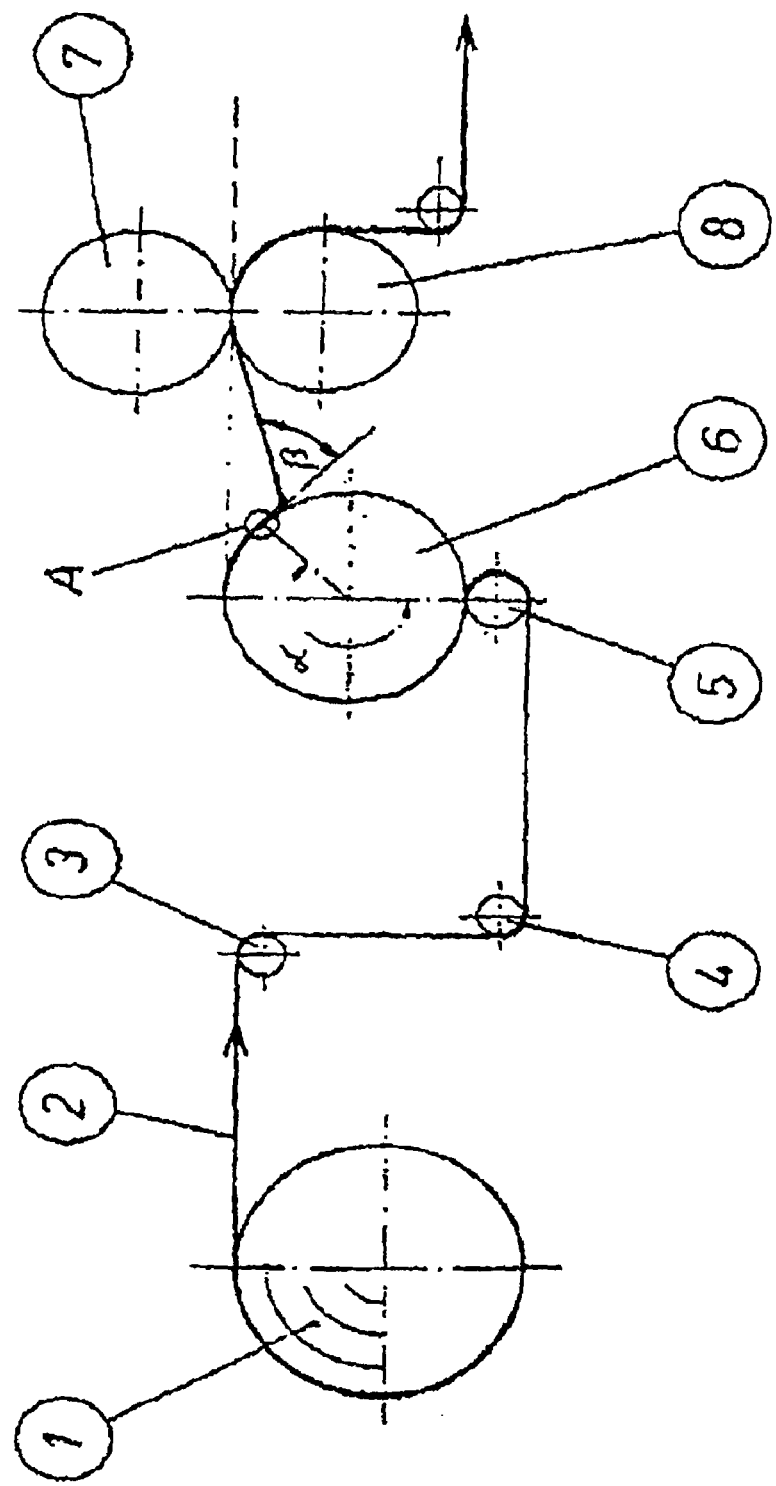

METHOD FOR PRODUCING A FILM WEB

RELATED APPLICATIONS

This application is the U.S. National Stage of International Application No. PCT/EP2006/003891, filed Apr. 26, 2006, published in German, and claims priority under 35 U.S.C. §119 or 365 to European Application No. 05009126.3, filed Apr. 26, 2005.

The invention relates to a process for the production of a film web, a film web produced therewith, as well as its use, in particular as hygiene film, for example diaper film or medical film.

Such hygiene films are preferably produced from polyolefins and have commonly a thickness from 5 to 40 µm. Due to their field of uses they must be liquid-impermeable. In this, for example, films for hygiene products are subjected to a whole series of further requirements. To these requirements there also belong the haptic properties of the film, for example, softness, suppleness, low rustling behavior and textile feel.

Films used in the field of hygiene should have a soft, fabric-like feel. In particular when used for incontinence products, the generation of noise should be as low as possible, i.e. the films should have a low rustling behavior. Together with a low level of gloss this results in a very textile film, which is very important in the field of hygiene.

In recent years, the absorption elements contained in diapers and incontinence products have become thinner and thinner, which has been made possible by the use of superabsorbent polymers. These superabsorbent polymers are used in the form of granular powders, and the hygiene films must have such strength that puncture of the film by the individual granules, for example during loading by sitting or other movement of the wearer, is reliably prevented. A formation of pinholes by superabsorbent polymers and a bursting of the final film products in the packaging units must be prevented. This requirement on the puncture resistance has to date limited the trend towards thinner hygiene films.

A further requirement of hygiene films consists in a minimum tensile strength which is necessary for processing of the film webs on the high-speed machines (converters) of the producers of, for example, diaper films and sanitary towels. This minimum tensile strength is expressed for 5%, 10% or 25% elongation in machine direction (md) or cross (transverse) direction (cd). Presently, the tensile strength at 5% elongation (5% modulus) in machine direction should be at least 3 N/inch. In addition, films used in hygiene applications should exhibit a transverse tear strength of at least 10 N/inch.

From DE-A-33 26 056 there is known a process for producing thermoplastic films, wherein a mass of LLDPE (linear low density polyethylene) is extruded in the form of a web using the slit die process, wherein the mass is maintained at a temperature above its melting temperature. The web is passed from the slit die to a tensioning roll along a tension gap defined in its length and then stretched to a is film by means of the tensioning roll. In this, the surface of the tensioning roll is kept at a temperature which causes solidification/crystallization of the film being on it. The described films have a thickness of 25 µm.

EP-A-0 616 880 describes a process for producing a film being suitable for packaging materials and being from a thermoplastic resin, wherein film thicknesses between 100 and 2000 µm are obtained. In this process, a thermoplastic starting film is heated to a temperature between its softening point and its melting point and then cooled.

From EP-A-0 768 168 there is known a process for producing a film web being useable in the field of hygiene, wherein a starting film web of thermoplastic polymer material is warmed until the polymer material is in the molten state and then passed through a cooled roll nip.

EP-A-0 256 885 discloses backsheets for diapers, which backsheets consist essentially of low density polyethylene and 10 to 20% by weight of polypropylene. In this, by the addition of polypropylene, inter alia, the adhesion properties to the tape used for closing the diaper ("tape adhesion") should be improved. The thickness of the described films is within the range of from 25 to 38 µm (1.0 to 1.5 mil). From GB-A-2 152 515 there are known films of polymer blends, wherein 2 to 15% by weight of polypropylene is added to polyethylene (LLDPE, LDPE), in order to increase stiffness. In GB-A-2 152 516 of the same applicant it is reported that films of LLDPE with an addition of polypropylene exhibit increased stiffness compared to films of LLDPE alone, however, such films "exhibit a catastrophic decrease in impact and tear strength in particular in the machine direction (md)". Therefore, GB-A-2 152 516 adds up to 2% by weight of specific elastomers. However, these elastomers are, on the one band, very difficult to extrude and, on the other hand, very expensive.

As mentioned in the introductory part, there are limits to the trend towards thinner and thinner hygiene films, in that for the processing of the film webs on the high-speed machines of the producers minimum requirements with regard to the mechanical properties have to be met, since otherwise a workmanlike processing can be no longer guaranteed or the processing products are accompanied by properties which are not accepted by the users. Minimum requirements consist, for example, with respect to tensile strength, tensile strength at 5%, 10% and 25% elongation, as well as elongation at break, in each case in machine direction (md) and cross direction (cd), as well as puncture resistance. Further minimum requirements consist with respect to softness and suppleness, respectively, of the film which should exhibit a feel being as textile as possible, and the rustling behavior, i.e., the generation of noise of the film should be as low as possible. In the conventional processes for producing film webs for the field of hygiene the minimum requirements of today are met up to film thicknesses of about 25 µm. Compared to this, the process according to EP-A-0 768 168 already brought an improvement, so that the film thickness could be decreased up to 23 µm and in some cases even more. The problem of the invention was to further improve the desired properties of the films, so that, in particular also for film thicknesses of 20 µm or even below, these minimum properties are met.

Thus, the subject-matter of the invention refers to a process for the production of a film web, wherein a starting film web of thermoplastic polymer material containing a polyethylene matrix containing 1 to 70 parts by weight of polypropylene, based on 100 parts by weight of polyethylene matrix, is passed, after warning, through a cooled roll nip, characterized in that the starting film web is warmed until the molten state of the polyethylene matrix material, but not until the molten state of the polypropylene. Further, the invention refers to film webs produced using this process as well as their use, in particular in the field of hygiene and medical field. Preferred embodiments of the invention are described in the following description, the FIGURE, the example and the dependent claims.

The process of the invention solves the problem set forth, i.e., it enables the production of commercially useable film webs with the desired properties, which webs exhibit a decreased film thickness of below 20 µm, e.g. 18 or 16 or even only 15 μm. A further advantage of the film webs obtained according to the process of the invention resides in an improved thermostability. When using the film webs as so called backsheets in the field of hygiene, the inner equipment of e.g. baby diapers or incontinence articles is applied by means of hot melt adhesive systems which are applied at temperatures in the range of from 140 to 160° C. in this, the desired properties of the backsheets may not be lost, what is, in case of the conventional backsheets, only possible when using larger film thicknesses.

As is known, polymers do not have a sharply defined melting point, but instead a melting range, although the crystalline regions of the polymer can be ascribed a crystalline melting point. This crystalline melting point is always higher than the melting point (range) of the non-crystalline constituents. In any case, the molten state is defined as the state where the shear modulus approaches zero and—in the case of polymers having crystalline regions—the latter are no longer detectable.

The shear modulus can be determined, for example, according to ISO 6721-1 & 2. In the present invention, the starting film web is warmed to a temperature at which the shear modulus for the polyethylene matrix material approaches zero and crystalline regions are no longer detectable. On the other hand, the shear modulus for the polypropylene does not approach zero and crystalline regions are still detectable. Thus, the shear modulus of the whole polymer material of the starting film web does not approach zero and crystalline regions of the polypropylene are still detectable.

The polyethylene matrix of the film web consists substantially of ethylene polymers, wherein both ethylene homopolymers and ethylene copolymers containing ethylene as main comonomer are suitable. Suitable ethylene homopolymers are LDPE (low density polyethylene). LLDPE (linear low density polyethylene), MDPE (medium density polyethylene), and HDPE (high density polyethylene). Preferred comonomers for ethylene copolymers are other olefins, with the exception of propylene, for example, butene, hexene, or octene. Preferably, the content of comonomer is below 20% by weight-%, in particular below 15% by weight.

In a preferred embodiment, the polyethylene matrix consists exclusively of ethylene homopolymers, e.g. blends of LDPE and LLDPE, which each may be contained in amounts of 10 to 90% by weight. A specific example is a polyethylene matrix of 60% by weight of LDPE and 40% by weight of LLDPE.

Beside the ethylene homo- or copolymers, the polyethylene matrix may further contain other thermoplastic polymers, wherein it has to be taken care that hereby the temperature at which the whole polymer matrix material is in the molten state does not approach too close to the temperature at which the polypropylene would be in the molten state, in this context see further below.

The starting film web contains 1 to 70 parts by weight of polypropylene in the polyethylene matrix, based on 100 parts by weight of polyethylene matrix. Preferably, the amount of polypropylene is 5 to 65 parts by weight, in particular 5 to 45 parts by weight and more preferably 10 to 40 parts by weight, in each case based on 100 parts by weight of polyethylene matrix. Specific examples for polypropylene amounts contained in the polyethylene matrix are 14, 16, 18, 25 or 28 parts by weight of polypropylene.

The expression polypropylene as used herein comprises both propylene homo- and copolymers containing propylene as main comonomer. In case of the propylene copolymers the percentage of comonomer, i.e. non-propylene, has to be ascribed to the polyethylene matrix according to the invention. Suitable comonomers for propylene copolymers are other olefins, preferably ethylene. In case of the propylene ethylene copolymers the percentage of ethylene is preferably 2 to 30% by weight, preferably 2 to 20% by weight and in particular 2 to 15% by weight, wherein in practice very good results are obtained when using a content of ethylene of 3 to 12% by weight. These numerical values also apply for the other olefins. Copolymers of polypropylene with ethylene are available as commercial products, for example for the production of blown and/or cast films.

In a specific embodiment, a starting film web of the following composition is used: polyethylene matrix of 40% by weight of an ethylene octene copolymer with a percentage of octene of 5 to 10% by weight, the remainder being LDPE; 5 to 45 parts by weight of propylene ethylene copolymer with 3 to 12% by weight of ethylene, based on 100 parts by weight of polyethylene matrix.

In the process of the invention the warming of the starting film web is carried out until the polyethylene matrix material is in the molten state, but not until the molten state of the polypropylene. It has already been set forth above, that polymers do not have a sharply defined melting point but instead a melting range, although the crystalline regions of the polymer can be ascribed a crystalline melting point, wherein in turn this crystalline melting point is always above the melting range of the non-crystalline regions. Below the melting ranges for some polyethylene matrix materials and polypropylene contained therein are given.

LDPE: 112-114° C.;
LLDPE: 119-125° C.;
Propylene homopolymers: 155-165° C.;
Propylene ethylene copolymers: 130-162° C., may be higher if very little ethylene is present.

In order to achieve the essential feature of the process of the invention, i.e. to warm the starting film web until the molten state of the polyethylene matrix, but not until the molten state of the polypropylene, there is provided a sufficient temperature distance, and, provided the above mentioned condition is met, the particularly selected temperature distance makes no particular difference, rather this is determined by practical considerations with respect to the safety of the process operation or by economic considerations. If, for example, the polymer matrix is clearly molten at a specific process temperature, a further increase in temperature does not result in better results. In addition, the heat consumption increases and, optionally, the melting range of the polypropylene is approached too close, so that it is more difficult to carry out the process. Preferably, therefore the process of the invention is carried out in such a manner that the warming of the starting film web is carried out until a temperature not higher than 10 to 15° C. below the crystalline melting point of the polypropylene.

The starting film webs used in the process of the invention may be colored, for example, white by means of titanium dioxide. In addition, the starting film webs may contain conventional additives and processing aids.

In the starting film webs used in the process of the invention the polypropylene is contained in a polyethylene matrix. During the production of the starting film web, for example using the slit die process or blowing process, in any case the blend of polyethylene matrix material and polypropylene has to be heated in the extruder until significantly above the melt flow temperature of all polymer constituents, e.g. until above 200° C., whereby a homogeneous mixing in the melt is achieved.

The thickness of the starting film web is, for example, within the range of from 5 to 40 μm, preferably 10 to 30 μm and more preferably 12 to 25 µm. The process according to the invention enables the production of films with low film thickness of e.g. 20, 18, 16 or even only 15 µm, which films nevertheless meet the requirements of hygiene films, in particular with respect to softness, rustling behavior and puncture resistance.

According to the invention the warming of the starting film web can be carried out in various ways. However, the warming is preferably carried out by means of one or more contact rolls/heating rolls heated to the prescribed temperature by means of a heat-transfer medium.

In order to ensure that the starting film web actually reaches the roll temperature, a sufficient residence time of the starting film web on the heating roll surface must be ensured. This can also be achieved by increasing the wrap angle α (see the FIGURE), by increasing the roll diameter and/or by reducing the film web speed in accordance with the film thickness.

In another embodiment, the warming of the starting film web takes place by means of radiation heat, either exclusively or in order to support warming by means of heating rolls.

A particular difficulty of processing the film web in the molten state of the polyethylene matrix by means of heating rolls is that the film web adheres to the heating rolls much more strongly than in the conventional processing at below the temperature of the molten state. This requires an increased detachment force. The increased adhesion of the film web to the heating roll also results in a shift in the detachment point in the direction of rotation of the heating roll, which in turn means an increase in the detachment angle β (see the FIGURE). The detachment force can increase here to such an extent that the film web tears. On the other hand, the increased adhesion can result in the partially molten film web not being detachable at all from the heating roll and rotating with the roll, and in this way production comes to a standstill. For this reason, a heating roll having a modified surface which has reduced adhesion to the partially molten film web is preferably used in accordance with the invention. To this end, a heating roll coated with PTFE (polytetrafluoroethylene) is preferably used. Other non-stick surfaces are also suitable.

The partially molten state of the film web on the heating roll results in delayed detachment of the film web in the direction of rotation of the heating roll. The extent of the delay is dependent on the process parameters and the film material and is defined by a detachment angle β. The smallest angular value (0°) is given by the tangent running from the cooled roll nip to the heating roll (indicated by the dashed line in the FIGURE), where the angle toward larger values is in principle limited only by the feed point of the starting film onto the heating roll. When carrying out the process in practice, however, detachment angles β of significantly greater than 90° are impractical, since loop or pocket formation of the partially molten film web on the heating roll can then occur.

According to the invention the starting film web is passed through a cooled roll nip after warming. The rolls forming the roll nip are cooled, for example by means of water in a temperature range of from 5 to 20° C., so that rapid cooling of the film web to a temperature below the crystalline melting point of the polyethylene matrix material, preferably 80° C. or below, is ensured. The distance between the final heating roll and the cooled roll nip should, owing to possible heat losses, not be excessively large. In any case, the minimum distance is limited by the dimensions of the rolls. The cooled roll nip can be, for example, smooth. However, in the case of hygiene films, the roll nip preferably is formed by a pair of rolls with structured roll, whereby the film web obtains a structured surface.

The film web speeds very within conventional limits, for example in the range of from 50 to 500 m/min, depending on the film parameters and the other process conditions.

The force necessary to detach the film web from the heating roll is applied by a pretension achieved by an increased web speed (overfeed) in the cooled roll nip compared with the web speed on the heating roll. In order to apply the detachment force, an overfeed of a few percent, for example 0.5 to 5% is sufficient. The overfeed can also be selected to be very much higher, for example if a reduction in the film thickness is to take place. For example, an overfeed of 30% results in a reduction in the film thickness from 30 to 20 µm.

The starting film webs used for carrying out the process of the invention can be produced in any manner, preferably they are produced by the slit die process, wherein a film is extruded through a slit die, or by the blowing process, the blowing process being preferred. When using the blowing and slit die processes the films are produced by extrusion in a known manner, wherein preferably care is taken of good mixing in the extruder. Preferably such films are used, which have been subjected to stretching in the transverse direction during production. Of these, preference is again given to blown film webs. The process of the invention is preferably carried out with single-layer film webs, but multi-layer film webs can also be used.

The FIGURE shows a preferred embodiment for carrying out the process according to the invention. From the reel 1, the starting film web 2 passes over deflection rolls 3 and 4 and a pressure roll 5 to the heating roll 6. The heating roll 6 is, for example, a steel roll which has a non-stick coating and is heated to the desired surface temperature by means of a heat-transfer medium. Then, the film web passes on the heating roll 6 and is warmed according to the invention. The wrap angle α is the angle formed from the first point of contact of the starting film web 2 with the heating roll 6 as far, regarded in the direction of rotation of the heating roll 6, as the point where the detachment of the film web from the heating roll takes place. From the heating roll 6, the film web passes at a detachment angle β (detachment point A) into a cooled roll nip formed by a pair of rolls 7 and 8. Preferably, the roll 8 is a structured roll, whereby the film web obtains a structured surface. The roll pair 7/8 is preferably water-cooled. The rolls 7 and 8 forming the nip can be driven at such a speed that there is an overfeed compared with the web speed on the heating roll 6, which results in a reduction in the film web thickness. After roll pair 7/8 the film web is taken off.

The invention enables the production of films which combine the mechanical and haptic properties required in the field of hygiene with simultaneously low film thickness. Therefore, good processability to the final products, e.g. diapers, on the conventional converters is possible and high safety against tearing down or tearing off of the final products and against the formation of pinholes is ensured. To this end, it is surprising that, despite of the content of polypropylene, a supple film with low generation of noise and sympathetically textile feel, but on the other hand superior mechanical properties, is obtained.

The invention will be illustrated by the following example.

EXAMPLE

A starting film web has been produced by the blowing process using a formulation as shown in Table I.

TABLE I

| Amount, parts by weight | Constituent | Density, g/cm³ | Crystalline melting point, °C. | Melt index, g/10 min[2] |
|---|---|---|---|---|
| 59 | LDPE | 0.922-0.924 | 113 | 0.60-0.90 |
| 41 | LLDPE-octene | 0.930 | 124 | 1.0 |
| 30 | polypropylene[1] | 0.90 | 162 | 0.4 |
| 5 | TiO₂-white concentrate | 1.69 | — | — |

[1] Propylene ethylene copolymer containing 10% by weight of ethylene
[2] 190° C./2.16 kg for LDPE and LLDPE, and 230° C./2.16 kg for polypropylene The conditions during blowing of the film tube are to be seen from the following Table II.

TABLE II

| Blowing conditions | |
|---|---|
| Annular die | 600 mm diameter |
| Die gap | 1 mm |
| Tube diameter | 1590 mm |
| Film thickness | 16 μm |
| Temperature of the extruder | 240° C. |

The film tube obtained was cut open in the longitudinal direction and wound up on two reels. The film width was 2.5 m.

This starting film web was subjected to the process shown in the FIGURE as follows. After taking off of the starting film web 2 from the reel 1, the film web passes over the deflection rolls 3, 4 and the pressure roll 5 to the heating roll 6. The heating roll 6 is a steel roll which has a non-stick coating and is heated to a surface temperature of 130° C. by means of a heat-transfer medium. The heating roll 6 is driven at a web speed of 260 nm/min. From the heating roll 6, the film web passes into a cooled roll nip formed by the roll pair 7/8. The roll 8 is a structured roll. The roll pair 7/8 is water-cooled (15° C.). The rolls 7/8 forming the nip are driven at such a speed that an overfeed of 5% (13 m/min) arises compared with the web speed on the heating roll 6 of 260 m/min. This overfeed results in a reduction in the film web thickness from 16 to 15 μm. A detachment angle β≧90° forms here. The wrap angle α is about 200° C.

In Table III the measurement values of this film (A) are compared with the measurement values of a film (B) obtained with the process of EP-A-0 768 168.

TABLE III

| Measured variable | | Measuring specification | Dimensions | Film A | Film B |
|---|---|---|---|---|---|
| Thickness | | | μm | 15 | 15 |
| Embossing height | | EN ISO 2286-3 | μm | 31 | 31 |
| Tensile strength at elongation of | | EN ISO 527 | N/inch | | |
| 5% | | | | 3.5 | 2.0 |
| 10% | md* | | | 4.8 | 3.2 |
| 25% | | | | 7.0 | 5.5 |
| Tensile strength at elongation of | | EN ISO 527 | N/inch | | |
| 5% | | | | 3.5 | 2.0 |
| 10% | cd* | | | 4.2 | 2.3 |
| 25% | | | | 4.3 | 2.5 |
| Tear strength | md | EN ISO 527 | N/inch | 19.0 | 14.0 |
| | cd | | | 13.0 | 9.0 |
| Elongation at | md | EN ISO 527 | % | 300 | 270 |
| break | cd | | | 700 | 700 |
| Gloss | | DIN 67530 | | 4.0 | 4.0 |
| Puncture resistance | | Internal specification, particularly for diapers | mm | 500 | 500 |

*md = in machine direction
cd = transverse to machine direction

After assessment by test persons, the films A and B exhibit the same sympathetic textile-like feel and the same rustling behavior. The puncture resistance of both films is also the same. On the other hand, film A shows, compared to film B, dramatic improvements with respect to tensile strength and tear strength.

The invention claimed is:

1. A process for the production of a film web suitable for use as a hygienic film, comprising the steps of:
    a) warming a starting film web of thermoplastic polymer material comprising a polyethylene matrix containing 1 to 70 parts by weight of polypropylene, based on 100 parts by weight of polyethylene matrix, to a temperature above the molten state of the polyethylene matrix, but below the molten state of the polypropylene to form a partially molten film web; wherein said starting film web is warmed by one or more heating rolls;
    b) passing the partially molten film web through a cooled roll nip, thereby forming the film web suitable for use as a hygiene film.

2. The process according to claim 1, characterized in that a starting film web containing 5 to 45 parts by weight of polypropylene, based on 100 parts by weight of polyethylene matrix, is used.

3. The process according to claim 2, characterized in that a starting film web containing 10 to 40 parts by weight of polypropylene, based on 100 parts by weight of polyethylene matrix, is used.

4. The process according to claim 1, characterized in that a starting film web containing a polyethylene matrix of 60% by weight of LDPE and 40% by weight of LLDPE is used.

5. The process according to claim 3, characterized in that a starting film web containing a polyethylene matrix of 60% by weight of LDPE and 40% by weight of LLDPE-octene with an amount of octene of 5 to 10% by weight, and an amount of 30 parts by weight of propylene ethylene copolymer containing 3 to 12% by weight of ethylene as comonomer, based on 100 parts by weight of polyethylene matrix, is used.

6. The process according to claim 1, wherein the starting film web of thermoplastic polymer material consists essentially of the polyethylene matrix and 1 to 70 parts by weight of the polypropylene, based on 100 parts by weight of the polyethylene matrix, wherein the polypropylene is a homopolymer or a copolymer of propylene and a second olefin.

7. The process according to claim 6, wherein the polypropylene is a copolymer of propylene and ethylene.

8. The process according to claim 1, characterized in that a starting film web having a thickness of from 10 to 30 μm is used.

9. The process according to claim 1, characterized in that heating rolls having reduced adhesion tendency to the film web with molten polyethylene matrix are used.

10. The process according to claim 1, characterized in that a starting film web which has been subjected during production to transverse stretching is used.

11. The process according to claim 1, characterized in that a film web having a thickness of from about 15 μm to about 20 μm is produced.

12. The process of claim 1, wherein the partially molten film web is cooled in the roll nip to a temperature below the crystalline melting point of the polyethylene matrix.

13. The process of claim 1, wherein the starting film web is warmed to a temperature not higher than 10 to 15° C. below the crystalline melting point of the polypropylene.

14. A film web obtained by a process according to claim 1.

15. The film web according to claim 14, having a thickness in the range of from 15 to 20 μm.

* * * * *